United States Patent [19]

Badger et al.

[11] Patent Number: 5,591,748
[45] Date of Patent: Jan. 7, 1997

[54] IMMUNOMODULATORY AZASPIRANES

[75] Inventors: Alison M. Badger; Gary J. Bridger, both of Bryn Mawr, Pa.; David A. Schwartz, Encinitas, Calif.

[73] Assignee: SmithKline Beecham Corporation, Philadelphia, Pa.

[21] Appl. No.: 277,456

[22] Filed: Jul. 19, 1994

Related U.S. Application Data

[63] Continuation-in-part of Ser. No. 981,147, Nov. 24, 1992, abandoned, which is a continuation of Ser. No. 712,325, Jun. 7, 1991, abandoned.

[51] Int. Cl.$^6$ .................. A61K 31/44; C07D 401/04; C07D 453/00
[52] U.S. Cl. .................. 514/278; 514/390; 514/409; 546/15; 546/16; 546/126; 546/133; 548/408
[58] Field of Search .................. 546/15, 16, 126, 546/133; 548/408; 514/278, 397, 409

[56] References Cited

U.S. PATENT DOCUMENTS

| | | | |
|---|---|---|---|
| 3,106,552 | 10/1963 | Grogan | 546/16 |
| 3,256,277 | 6/1966 | Rice et al. | 544/70 |
| 3,282,947 | 11/1966 | Rice et al. | 546/16 |
| 3,326,925 | 6/1967 | Giudicelli et al. | 546/16 |
| 3,418,324 | 12/1968 | Rice et al. | 546/17 |
| 3,432,499 | 3/1969 | Rice et al. | 546/16 |
| 3,825,546 | 7/1974 | Rice et al. | 546/4 |
| 3,907,801 | 9/1975 | Wu | 546/16 |
| 4,468,393 | 8/1984 | Geschickter et al. | 514/184 |
| 4,654,333 | 3/1987 | Tenoso et al. | 514/184 |

FOREIGN PATENT DOCUMENTS

| | | |
|---|---|---|
| WO85/05031 | 11/1985 | Australia . |
| 186505A2 | 7/1986 | European Pat. Off. . |
| 0310321A2 | 4/1989 | European Pat. Off. . |
| 823338 | 11/1959 | United Kingdom . |
| 929739 | 6/1963 | United Kingdom . |

OTHER PUBLICATIONS

Dorland's "Medical dictionary" W. B. Saunders Co. Pubr. pp. 423, 825 (1994).
Rice, et al. Heterocycl. Chem., 10(5) 731–735 (1973).
Rice, et al. Heterocycl. Chem., 10(5) 737–741 (1973).
Rice, et al. J. Med. Chem., 6, 338–402 (1963).
Rice, et al. J. Heterocycl., Chem., 1(3), 125–127 (1964).
DiMartino, et al. J. Pharmacol. Exp. Therapeut., 236, 103–110 (1986).
Badger, et al. Immunopharmacol., 10, 201–207 (1985).

*Primary Examiner*—Ceila Chang
*Attorney, Agent, or Firm*—Wayne J. Dustman; Stephen Venetianer; Edward T. Lentz

[57] ABSTRACT

Invented are substituted azaspirane compounds, pharmaceutical compositions containing these compounds, and methods for using these compounds to induce an immunosuppressive effect in a mammal in need thereof.

8 Claims, No Drawings

IMMUNOMODULATORY AZASPIRANES

This is a continuation-in-part of application Ser. No. 07/981,147, filed Nov. 24, 1992; now abandoned, which is a continuation of application Ser. No. 07/712,325, filed Jun. 7, 1991, now abandoned.

FIELD OF THE INVENTION

The present invention relates to certain novel substituted azaspirane compounds, pharmaceutical compositions containing these compounds, and methods for using these compounds to induce an immunomodulatory effect in a mammal, including a human, in need thereof.

BACKGROUND OF THE INVENTION

Azaspirane derivatives, processes for their preparation and methods of their use have been described. Geschickter et al., U.S. Pat. No. 4,468,393, issued Aug. 28, 1984.

Tenoso et al., U.S. Pat. No. 4,654,333, issued Mar. 31, 1987.

Rice et al., *J. Heterocycl. Chem.*, 10 (5), 731–735 (1973).

Rice et al., *J. Heterocycl, Chem.*, 10 (5), 737–741 (1973).

Rice et al., U.S. Pat. No. 3,256,277, issued Jun. 14, 1966.

Rice et al., U.S. Pat. No. 3,282,947, issued Nov. 1, 1966.

Rice et al., *J. Med. Chem.*, 6, 388–402 (1963).

Rice et al., *J. Heterocycl. Chem.*, 1(3), 125–127 (1964).

Rice et al., U.S. Pat. No. 3,825,546, issued Jul. 23, 1974.

DiMartino et al., *J. Pharmacol. Exp. Therapeut.*, 236, 103–110 (1986).

Badger et al., *Immunopharmacol.*, 10, 201–207 (1985).

Geschickter Fund, British Patent Application Number 929,739, published Jun. 26, 1963.

A full text of the background of the invention as described above was published in Badger, et al. U.S. Pat. No. 4,963,557, issued Oct. 16, 1990.

SUMMARY OF THE INVENTION

The present invention resides in the discovery that certain novel substituted azaspirane analogues induce an immunomodulatory effect, in a mammal, including a human, in need thereof and are potent immunomodulatory agents.

Presently, preferred compounds of the invention and compounds used in the invented pharmaceutical compositions and in the invented methods include:

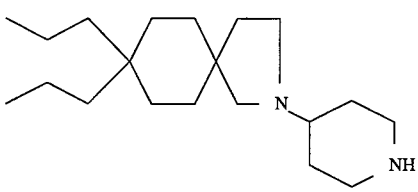

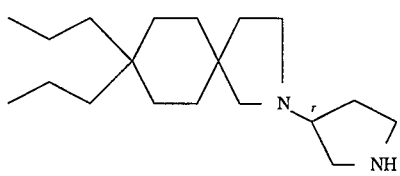

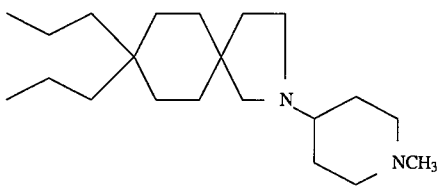

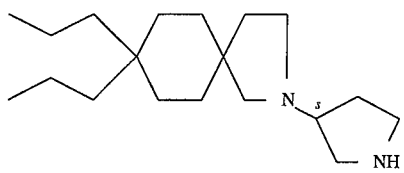

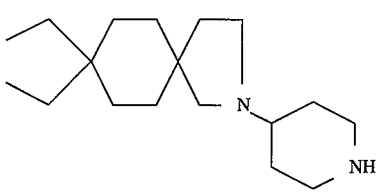

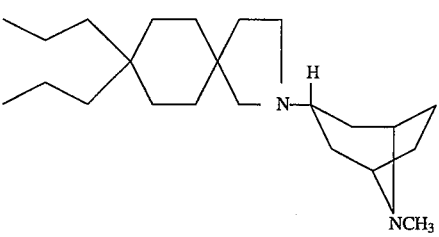

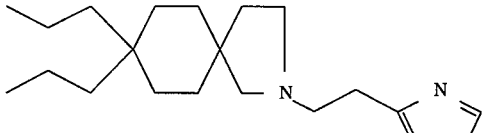

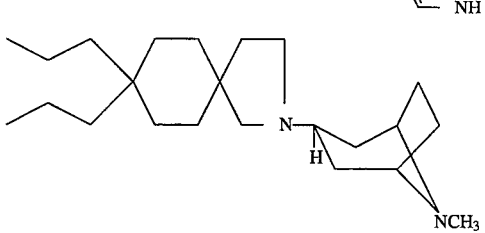

and

The invention also is a method for inducing suppressor cell activity in mammals, including humans, that comprises administering to a subject in need thereof an effective amount of a presently invented immunomodulating compound.

Included in the present invention are pharmaceutical compositions comprising a pharmaceutical carrier and compounds useful in the methods of the invention.

DETAILED DESCRIPTION OF THE INVENTION

The presently invented compounds that are potent immunomodulatory agents have the following formula (I):

in which:

$R^1$ and $R^2$ are the same or different and are selected from hydrogen or straight chain, branched chain or cyclic alkyl, provided that the total number of carbon atoms contained by $R^1$ and $R^2$ when taken together is 4–10; or $R^1$ and $R^2$ are joined together to form a cyclic alkyl group containing 3–7 carbon atoms;

A is absent or present as $C_1$–$C_7$alk; and $R^3$ is a heterocyclic ring selected from; pyrrolidine, piperidine, imidazole and azabicyclo(3.2.1),wherein said heterocyclic ring is bonded through a carbon atom thereof and wherein each nitrogen atom of said heterocyclic ring is optionally substituted by a substituent selected from; hydrogen, $-CH_3$, $-CH_2-CH_3$, $-CH(CH_3)_2$ and $-CH_2-CH_2-CH_3$; provided that such nitrogen atoms are not substituted when they form part of a double bond or when they are attached to three carbon atoms in a azabicyclo(3.2.1.) ring system; or a pharmaceutically acceptable salt, hydrate or solvate thereof.

A preferred group of the invented compounds are those of Formula (I) where:

$R^1$ and $R^2$ are each independently $C_2$ or $C_3$ alkyl;

A is absent or present as $C_1$–$C_2$alk; and $R^3$ is a heterocyclic ring selected from; pyrrolidine, piperidine, imidazole and azabicyclo(3.2.1),wherein said heterocyclic ring is bonded through a carbon atom thereof and wherein each nitrogen atom of said heterocyclic ring is optionally substituted by a substituent selected from; hydrogen, $-CH_3$, $-CH_2-CH_3$ and $-CH_2-CH_2-CH_3$; provided that such nitrogen atoms are not substituted when they form part of a double bond or when they are attached to three carbon atoms in a azabicyclo(3.2.1.) ring system; or a pharmaceutically acceptable salt, hydrate or solvate thereof.

Additionally, preferred among the presently invented compounds are those of Formula (I) where:

$R^1$ and $R^2$ are each independently $C_2$ or $C_3$alkyl;

A is absent or present as $C_1$–$C_2$alk; and $R^3$ is a heterocyclic ring selected from; pyrrolidine, piperidine, imidazole and azabicyclo(3.2.1),wherein said heterocyclic ring is bonded through a carbon atom thereof and wherein each nitrogen atom of said heterocyclic ring is optionally substituted by a substituent selected from; hydrogen, and $-CH_3$; provided that such nitrogen atoms are not substituted when they form part of a double bond or when they are attached to three carbon atoms in a azabicyclo(3.2.1.) ring system; or a pharmaceutically acceptable salt, hydrate or solvate thereof.

Preferred heterocyclic rings for use herein are those in which at least one of said nitrogens is positioned with three carbon atoms between the subject heteroatom and the 2-aza substituent.

As used herein, unless otherwise specified $C_{1-n}$alk and $C_{1-n}$alkyl means a straight or branched hydrocarbon chain having 1-n carbons.

Compounds of Formula (I) are included in the pharmaceutical compositions and used in the methods of the invention.

The compounds of this invention are prepared by procedures described here below and illustrated by the examples. Reagents, protecting groups and functionality of the molecule must be consistent with the proposed chemical transformations. Steps in the synthesis must be compatible with the functional groups and the protecting groups.

Formula (I) compounds are prepared as described in Scheme I where $R^1$, $R^2$, $R^3$ and A are as defined in Formula I and the definition of $R^3$ additionally comprises protecting groups, preferably benzyl protecting groups, which are dissociated to prepare the substituents of $R^3$ as defined in Formula I or are dissociated and further reacted to prepare the substituents of $R^3$ as defined in Formula I.

SCHEME I

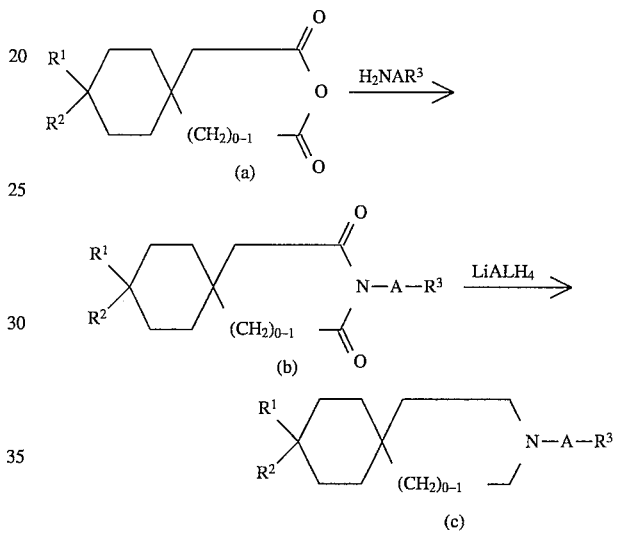

Scheme I depicts formation of Formula (I) compounds. The starting anhydride compounds are known and are synthesized from available precursors using known procedures. According to Scheme I, a solution of an anhydride compound (a) and a substituted primary amine compound are added to an appropriate organic solvent, preferably xylene or toluene, to form a reaction mixture. This reaction mixture is stirred at reflux with constant water removal, and evaporated to form formula (b) compounds.

Formula (c) compounds are prepared by adding to a formula (b) compound dissolved in a suitable organic solvent, such as tetrahydrofuran (THF), a suitable reducing agent, preferably, lithium aluminum hydride.

Pharmaceutically acceptable salts and their preparation are well known to those of skill in the art. Preferred pharmaceutically acceptable salts for basic compounds of Formula (I) include, but are not limited to, hydrochloride, citrate, maleate, lactate, hydrobromide, and sulfate.

The compounds of Formula (I) may form hydrates or solvates. It is known to those of skill in the art that charged compounds form hydrated species when lyophilized with water, or form solvated species when concentrated in a solution with an appropriate organic solvent.

All the compounds of Formula (I) are useful for treating an mammal, including humans, in need of immunomodulation. Such immunomodulatory activity was ascertained utilizing either the suppressor cell activity assay described by Badger et al., *Immunopharmacology* 10, 201–207 (1985) or the colony stimulating activity assay described below.

In the suppressor cell activity assay male inbred Lewis rats were obtained from Charles River Breeding Laboratories (Wilmington, Mass., U.S.A.). Rats were maintained on water and routine rat chow and were used at 6 to 8 weeks of age (160–180 g). Within any given experiment only rats of the same age, strain and sex were used. Concanavalin A (Con A) was obtained from Pharmacia Fine Chemicals (Piscataway, N.J.) and dissolved in a tissue culture medium (RPMI-1640, Flow Laboratories, Rockville, Md.) that was supplemented with penicillin, streptomycin and L-glutamine (Grand Island Biological Co., Grand Island, N.Y.) and with 10% heat-inactivated (56° C., 30 min) fetal calf serum. This medium will hereafter be referred to as RPMI-10. For in vivo treatment, compounds were dissolved in 0.5% tragacanth and administered orally once a day. Spleen cells from animals treated with compounds of Formula (I) were established in RPMI-10 at $5\times10^6$/ml. Co-culture experiments for the determination of suppressor cells were carried out by first adding varying numbers of the putative suppressor cells (0.15 to $5\times10^5$) to 96-well round bottomed microtiter plates (Linbro, Flow Labs) in 100 µl of RPMI-10. These cells were then irradiated (2000 Rad) in a Gamma cell 40 with a 137Cs source. To these cultures were added $5\times10^5$ normal cells and an optimal concentration of Con A (5 µg/ml) and the final volume was adjusted to 200 µl. Cell cultures were incubated for 72 hours at 37° C. in a 5% $CO_2$ atmosphere and pulsed with 0.5 µCi [$^3$H]thymidine (specific activity 1.9 Ci/mmol; schwarz/Mann, Orangeburg, N.Y.) for the last 16 hours of culture. The cells were harvested on an automated multiple sample harvester and cell-associated radioactivity counted in a Beckman liquid scintillation counter. Significant, suppressor cell activity is determined by comparing $^3$H-thymidine incorporation (cpm) of co-cultures containing untreated cells with those containing treated cells by Student's t test.

Suppressor cell activity is calculated in the following manner. A plot of percent suppression (dependent variable) versus the logarithm (base e) of the number of suppressor cells (independent variable) was generated and the area under the curve (AUC) represented by the data points of this plot was determined via the trapezoidal rule. The trapezoidal rule provides AUC by means of the summation of the areas of the trapezoids whose vertices are located at adjacent values of the independent variable and the corresponding values of the dependent variable. Data from AUC is represented as units of suppression. N,N-Dimethyl-8,8-dipropyl-2-azaspiro[4.5]decane-2-propanamine dihydrochloride (Compound A) is disclosed and claimed in Badger et al., U.S. Pat. No. 4,963,557 as a potent suppressor cell inducing immunomodulatory agent which exhibits an activity of 172 units in the suppressor cell activity assay at 30 mg/kg. (See, table II, column 9, compound 2).

Suppressor cell inducing compounds have also been associated with a transient hematopoietic effect (King, et al.) *Int. J. Immunopharmac.*, 13, No. 1, 91–100 (1991) (King I). One indicator of hematopoietic stimulation is an increase in serum colony stimulating activity (King I). As such, the suppressor cell inducing potential of compounds can be readily ascertained by utilizing the colony stimulating activity assay described below.

In the colony stimulating activity assay, mice (C57BL Females, Jackson Laboratories, ME) are given either an oral or I.P. injection (mg/kg) of either PBS or compound to be investigated. Blood is removed 6 hours later and placed in a non-heparinized tube. Blood is spun at 2000 RPM for 20 minutes to separate the serum. Varying dilutions of serum are then added to the NFS-60 cell line (murine IL-3-dependent myeloid cell line that responds to colony stimulating factors). The proliferative response to serum colony stimulating activity is determined by measuring 3H-thymidine incorporation during the last 6 hours of a 24-hour culture period.

For the comparison of azaspirane analogs, a program was developed that could be used to compare the colony stimulating activity generated in different experiments and the activities of different compounds. This was calculated in the following manner. A plot of percent stimulation (dependent variables) was generated, and the area under the curve (AUC), represented by the data points of this plot, was determined by the trapezoidal rule. The trapezoidal rule provides AUC by means of the summation of the areas of the trapezoids whose vertices are located in the adjacent values of the independent variable. Data from AUC is represented as units of stimulation. Serum from mice treated with a single I.P. injection of Compound A (30 mg/kg) contains 1655 units of colony stimulating activity by this method (mean value derived from four experiments).

Compounds within the scope of this invention have been tested and have been shown to have activity from 109–248 units in the suppressor cell activity assay (at 30 mg/kg) and from 592 to 2000 units in the colony stimulating activity assay (at 30 mg/kg). Compounds within the scope of this invention are potent immunomodulatory agents.

By "generating suppressor cells", "suppressor cell inducing" or "inducing suppressor cell activity" is meant that the compound induces a suppressor cell-like activity, e.g., a cell that is capable of suppressing the immune function of a normal cell in an in vitro co-culture assay such as that of Rich and Pierce, *J. Exp. Med.*, 137, 649 (1973). The spleen cells from treated animals were established at varying concentrations with normal cells. These suppressor cells are also capable of inhibiting mixed lymphocyte reactions, antibody synthesis and delayed-type hypersensitivity responses.

Compounds that induce suppressor cell activity have also been shown to inhibit the production of cytokines, particularly to inhibit the production of interleukin-1 (IL-1) and to inhibit the production of tumor necrosis factor (TNF), in Badger et al. WO 92/14462.

Biological activities attributed to IL-1 are disclosed in WO 92/14462 and are summarized in Table A below.

TABLE 1

Biological Activities Attributed to IL-1

Fever (in rabbits, mice and rats)

Hypoferremia

Hypozincemia

Hypercupremia

Increased

Blood neutrophils

Hepatic acute-phase proteins

Bone resorption, including; osteoprosis and Paget's disease

Cartilage breakdown

Muscle proteolysis

Slow-wave sleep

Endothelial procoagulant

Chondrocyte proteases

Synovial collagenase

Endothelial neutrophil adherence

Neutrophil degranulation

Neutrophil superoxide

Interferon production
Proliferation of
 Fibroblasts
 Glial cells
 Mesangial cells
 Synovial fibroblasts
 EBV B-cell lines
Chemotaxis of
 Monocytes
 Neutrophils
 Lymphocytes
Stimulation of $PGE_2$ in
 Hypothalamus
 Cortex
 Skeletal muscle
 Dermal fibroblast
 Chondrocyte
 Macrophage/monocyte
 Endothelium ($PGI_2$)
Decreased
 Hepatic albumin synthesis
 Appetite
 Brain binding of opioids
Augmentation of
 T-cell responses
 B-cell responses
 NK activity
 IL-2 production
 Lymphokine production.

The discovery of a compound which inhibits IL-1 production provides a therapeutic approach for diseases in which excessive or unregulated IL-1 production is implicated.

Badger et al. WO 92/14462 also discloses various mammalian conditions for which TNF is implicated in mediating or exacerbating. These conditions include: rheumatoid arthritis, rheumatoid spondylitis, osteoarthritis, gouty arthritis and other arthritic conditions; sepsis, septic shock, endotoxic shock, gram negative sepsis, toxic shock syndrome, adult respiratory distress syndrome, malaria, pulmonary inflammatory disease, bone resorption diseases, reperfusion injury, graft vs. host reaction, fever and myalgias due to infection, such as influenza, keloid formation, scar tissue formation, Crohn's disease, ulcerative colitis, or pyresis.

Compounds within the scope of this invention, as suppressor cell inducing agents, also have utility for inhibiting the production of cytokines, particularly IL-1 and TNF.

By the term "cytokine" as used herein is meant any secreted polypeptide that affects the functions of other cells, and is a molecule which modulates interactions between cells in the immune or inflammatory response. A cytokine includes, but is not limited to monokines and lymphokines regardless of which cells produce them. For instance, a monokine is generally referred to as being produced and secreted by a mononuclear cell, such as a macrophage and/or monocyte but many other cells produce monokines, such as natural killer cells, fibroblasts, basophils, neutrophils, endothelial cells, brain astrocytes, bone marrow stromal cells, epideral keratinocytes, and β-lymphocytes. Lymphokines are generally referred to as being produced by lymphocyte cells. Examples of cytokines include, but are not limited to, interleukin-1 (IL-1), tumor necrosis factor-alpha (TNFα) and tumor necrosis factor beta (TNFβ).

By the term "cytokine production inhibiting amount" as used herein is meant an effective amount of a compound of Formula (I) which will, when given for the treatment, prophylactically or therapeutically, of any disease state which is exacerbated or caused by excessive unregulated cytokine production, cause a decrease in the in vivo levels of the cytokine to normal or below normal levels.

By the term "inhibiting the production of cytokines" as used herein is meant:

a) a decrease of excessive in vivo cytokine levels in a mammal, including a human, to normal levels or below normal levels by inhibition of the in vivo release of cytokines by all cells, including but not limited to monocytes or macrophages;

b) a down regulation, at the level of transcription or translation, of excessive in vivo cytokine levels in a mammal, including a human, to normal levels or below normal levels; or c) a down regulation, by inhibition of the direct synthesis of a cytokines as a postranslational event.

Compounds that induce suppressor cell like activity have also been shown to synergistically combine with non-suppressor cell inducing immunosuppressive compounds to produce potent immunomodulatory agents in Badger, WO 92/02229. Compounds within the scope of this invention, as suppressor cell inducing immunomodulatory agents, also have utility for synergistically inducing immunosuppressive activity in a mammal, including a human, in need thereof when therapeutically combined with a non-suppressor cell inducing immunosuppressive compound.

This invention also relates to a pharmaceutical composition comprising a pharmaceutically acceptable carrier or diluent and an effective amount of a compound of Formula (I).

A compound of Formula (I) is administered in conventional dosage form prepared by combining a therapeutically effective amount (i.e., an effective immunomodulatory amount) of a compound of Formula (I) ("active ingredient") with standard pharmaceutical carriers or diluents according to conventional procedures. These procedures may involve mixing, granulating and compressing or dissolving the ingredients as appropriate to the desired preparation.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time delay material well known to the art, such as glyceryl monostearate or glyceryl distearate alone or with a wax, ethylcellulose, hydroxypropylmethylcellulose, methylmethacrylate and the like.

A wide variety of pharmaceutical forms can be employed. Thus, if a solid carrier is used, the preparation can be tableted, placed in a hard gelatin capsule in powder or pellet form or in the form of a troche or lozenge. The amount of solid carrier will vary widely but preferably will be from about 25 mg to about 1 g. If a liquid carrier is used, the preparation will be in the form of a syrup, emulsion, soft gelatin capsule, sterile injectable solution or suspension in an ampule or vial or nonaqueous liquid suspension.

To obtain a stable water soluble dose form, a compound of Formula (I) is dissolved in an aqueous solution of an organic or inorganic acid, such as a 0.3M solution of succinic acid, or, preferably, citric acid. Additionally, the compound of Formula (I) is dissolved in a suitable cosolvent or combinations thereof. Examples of such suitable cosolvents include, but are not limited to, alcohol, propylene glycol, polyethylene glycol 300, polysorbate 80, glycerin and the like in concentrations ranging from 0–60% of the total volume.

Preferably, each parenteral dosage unit will contain the active ingredient in an amount of from about 0.1 mg to about 500 mg. Preferably each oral dosage unit will contain the active ingredient in an amount of from about 1 mg to about 1000 mg.

The topical formulations of the present invention, both for veterinary and for human medical use, comprise an active ingredient together with one or more acceptable carrier(s) therefore and optionally any other therapeutic ingredient(s). The carrier(s) must be 'acceptable' in the sense of being compatible with the other ingredients of the formulation and not deleterious to the recipient thereof.

Formulations suitable for topical administration include liquid or semi-liquid preparations suitable for penetration through the skin to the site of where treatment is required such as: liniments, lotions, creams, ointments or pastes, and drops suitable for administration to the eye, ear or nose.

Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent. The resulting solution may then be clarified by filtration, transferred to a suitable container which is then sealed and sterilized by autoclaving or maintaining at 90°–100° C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powered form, alone or in solution or suspension in an aqueous or non-aqueous fluid, with the aid of suitable machinery, with a greasy or non-greasy basis. The basis may comprise hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as stearic or oleic acid together with an alcohol such as propylene glycol or macrogols. The formulation may incorporate any suitable surface active agent such as an anionic, cationic or non-ionic surfactant such as sorbitan esters or polyoxyethylene derivatives thereof. Suspending agents such as natural gums, cellulose derivatives or inorganic materials such as silicaceous silicas, and other ingredients such as lanolin, may also be included.

The compounds of Formula (I) are all active as immunomodulatory agents in mammals, including humans, in need of such immunomodulation when such compounds are administered to such mammals according to the method of this invention. By the term "immunomodulatory", "immunomodulatory agent" or "immunomodulatory compound" as used herein is meant that each of the compounds of Formula (I) is capable of inducing immune suppression via induction of suppressor cell-like activity (as evidenced by their activity in the suppressor cell activity assay and/or in the suppressor cell activity assay and in the colony stimulating activity assay described above). Indications for therapy using an immunomodulatory agent include, but are not limited to, the treatment of the following disease states:

rheumatoid arthritis systemic lupus erythematosis multiple sclerosis acute organ or bone marrow transplantation/graft rejection myasthenia gravis progressive systemic sclerosis multiple myeloma atopic dermatitis hyperimmunoglobin E hepatitis B antigen negative chronic active hepatitis Hashimoto's thyroiditis Familial Mediterranean fever Grave's disease autoimmune hemolytic anemia primary biliary cirrhosis inflammatory bowel disease insulin dependent diabetes mellitus This invention also relates to use of a compound of Formula (I) in treating an mammal in need of immunomodulation, including humans and other mammals, which comprises administering to such mammal an effective amount of a Formula (I) compound or a pharmaceutically acceptable salt, hydrate or solvate. By the term "treating" is meant prophylactic or therapeutic therapy. The Formula (I) compound is administered to an mammal in need of immunomodulatory treatment in an amount sufficient to produce such immunomodulation to a therapeutic or prophylactic degree. Such Formula (I) compound can be administered to such mammal in a conventional dosage form prepared by combining the Formula (I) compound with a conventional pharmaceutically acceptable carrier or diluent according to known techniques. It will be recognized by one of skill in the art that the form and character of the pharmaceutically acceptable carrier or diluent is dictated by the amount of active ingredient with which it is to be combined, the route of administration and other well-known variables.

The route of administration of the Formula (I) compound may be oral, parenteral, by inhalation or topical. The term parenteral as used herein includes intravenous, intramuscular, subcutaneous, rectal, vaginal or intraperitoneal administration. The subcutaneous and intramuscular forms of parenteral administration are generally preferred. The daily parenteral dosage regimen for a compound will preferably be from about 0.1 mg to about 1,000 mg per day. The daily oral dosage regimen will preferably be from about 1 mg to about 2,000 mg.

The compounds for Formula (I) may also be administered by inhalation. By "inhalation" is meant intranasal and oral inhalation administration. Appropriate dosage forms for such administration, such as an aerosol formulation or a metered dose inhaler, may be prepared by conventional techniques. The preferred daily dosage amount of a compound of Formula (I) administered by inhalation is from about 10 mg to about 100 mg per day.

The compounds of Formula (I) may also be administered topically.

The amount of a compound of Formula (I) (hereinafter referred to as the active ingredient) required for therapeutic effect on topical administration will, of course, vary with the compound chosen, the nature and severity of the inflammatory condition and the mammal undergoing treatment, and is ultimately at the discretion of the physician. A suitable immunomodulatory dose of a compound of Formula (I) is 1.5 mg to 500 mg of base per kilogram bodyweight for topical administration, the most preferred dosage being 1 mg to 50 mg/kg of mammal bodyweight, for example 5 mg to 25 mg/kg; administered two or three times daily. For application to the skin, from 1 mg to 500 mg of active ingredient may be applied per application, preferably from 10 mg to 100 mg per application.

By topical administration is meant non-systemic administration and includes the application of a compound of Formula (I) externally to the epidermis, to the buccal cavity and instillation of such a compound into the ear, eye and nose, and where the compound does not significantly enter the blood stream. By systemic administration is meant oral, intravenous, intraperitoneal and intramuscular administration.

While it is possible for an active ingredient to be administered alone, it is preferable to present it as a pharmaceutical formulation. The active ingredient may comprise, for topical administration, from 0.001% to 10% w/w, e.g. from 1% to 2% by weight of the formulation although it may comprise as much as 10% w/w but preferably not in excess of 5% w/w and more preferably from 0.1% to 1% w/w of the formulation.

It will be recognized by one of skill in the art that the optimal quantity and spacing of individual dosages of the Formula (I) compound will be determined by the nature and extent of the condition being treated, the form, route and site of administration, and the particular mammal being treated, and that such optimums can be determined by conventional techniques. It will also be appreciated by one of skill in the art that the optimal course of treatment, i.e., the number of doses of the Formula (I) compound given per day for a defined number of days, can be ascertained by those skilled in the art using conventional course of treatment determination tests.

Without further elaboration, it is believed that one skilled in the art can, using the preceding description, utilize the present invention to its fullest extent. The following Examples are, therefore, to be construed as merely illustrative and not a limitation of the scope of the present invention in any way.

I. SYNTHETIC EXAMPLES

In the following Examples, temperature is in degrees Centigrade (°C.). 4,4-Dipropylcyclohexane-1-carboxy-1-acetic acid anhydride, 4,4-diethylcyclohexane-1-carboxy-1-acetic acid anhydride, 4,4-dipropylcyclohexane-1,1-diacetic acid anhydride, and 4,4-diethylcyclohexane-1,1-diacetic acid anhydride were synthesized as described in U.S. Pat. No. 4,963,557. 4-Amino-1-benzylpiperidine, lithium aluminum hydride and tropinone were purchased from the Aldrich Chemical Co. (Milwaukee, Wis.). 3R-Pyrrolidine and 3S-pyrrolidine were purchased from CTC Organics (Atlanta, Ga.).

EXAMPLE 1

2-[4-Piperidinyl]-8,8-dipropyl-2-azaspiro[4,5]-decane dihydrochloride (i) 2-[4-(N-Benzyl)piperidinyl]-8,8-dipropyl-2-azaspiro [4,5]-decane-1,3-decane To a solution of 4,4-dipropylcyclohexane-1-carboxy-1-acetic acid anhydride (1 molar equivalent) in xylene was added 4-amino-1-benzylpiperidine (1 molar equivalent). The reaction mixture was heated at reflux with a Dean-Stark trap until 1 equivalent of water was collected in the trap. The reaction mixture was cooled to room temperature and concentrated under reduced pressure to give a white solid. The crude imide was dissolved in excess ethyl acetate followed by two washes with saturated aqueous sodium bicarbonate solution to remove any residual acid-amide from the product. The organic phase was dried over sodium sulfate, filtered, and concentrated to give the desired imide as a white solid; mp 148°–149° C.; 90–95% yield.

(ii) 2-[4-(N-Benzyl)piperidinyl]-8,8-dipropyl-2-azaspiro [4.5]-decane

To a mixture of lithium aluminum hydride (3.2 molar equivalents) in tetrahydrofuran was added dropwise a solution of 2-[4-(N-benzyl)piperidinyl]-8,8-dipropyl-2-azaspiro [4.5]-decane-1,3-dione (1 molar equivalent) in tetrahydrofuran. The reaction mixture was stirred for 2–6 h following completion of addition. The excess hydride was quenched with sodium sulfate-decahydrate and the resulting mixture was filtered and the filtrate was concentrated to give the desired diamine as a viscous, colorless oil. The oil was used directly without further purification; yield 90–95%.

(iii) 2-(4-Piperidinyl)-8,8-dipropyl-2-azaspiro[4.5]-decane

To a suspension of 10% palladium-on-carbon (0.1 molar equivalents) in a 7.5% formic acid in methanol solution was added 2-[4-(N-benzyl)piperidinyl]-8,8-dipropyl-2-azaspiro [4.5]-decane (1 molar equivalent). The reaction mixture was hydrogenated at 60 psi hydrogen pressure in a Parr hydrogenation apparatus at room temperature until hydrogen uptake had ceased (48–96h). The catalyst was removed by filtration through celite and the filtrate concentrated under reduced pressure. The residue was dissolved in water and then basified with 10% NaOH. The resulting aqueous emulsion was extracted with ethyl ether. The organic phase was dried over sodium sulfate, filtered and concentrated to give the debenzylated diamine product as a colorless oil; 90–95% yield.

(iv) 2-(4-Piperidinyl)-8,8-dipropyl-2-azaspiro[4.5]-decane dihydrochloride 2-(4-Piperidinyl)-8,8-dipropyl-2-azaspiro[4.5]decane was dissolved in a minimum of anhydrous ethanol and added to a cooled solution of hydrogen chloride in ethanol. On addition of a large volume of ether, a white precipitate formed which was isolated by filteration. The white solid was recrystallized from ethanol or methanol; mp 298°–300° C.; yield 85–90%.

EXAMPLE 2

2-(4-(N-Methyl)piperidinyl)-8,8-dipropyl-2-azaspiro[4.5]-decane dihydrochloride (i) 2-(4-(N-Methyl)piperidinyl-8,8-dipropyl-2-azaspiro [4.5]-decane To a solution of 2-(4-piperidinyl)-8,8-dipropyl-2azaspiro [4.5]-decane (1 molar equivalent prepared according to Example 1 (iii)) in acetonitrile was added 37% aqueous formaldehyde (5 molar equivalents) and sodium cyanoborohydride (1.6 molar equivalents). The reaction mixture was stirred overnight at room temperature. Added 2N KOH and extracted the reaction mixture twice with ethyl acetate. The combined organic extracts were washed with brine, dried over sodium sulfate, filtered and concentrated to give a yellow viscous oil. The residue was purified by chromatography on silica gel using MeOH/ethyl acetate/conc. ammonium hydroxide (74/24/1.5) as eluant. The product was isolated as a colorless oil; yield 60%.

(ii) 2-(4-N-Methyl)piperidinyl-8,8-dipropyl-2-azaspiro [4.5]-decane dihydrochloride The title compound is prepared according to Example 1 (iv) by substituting 2-(4-(N-Methyl)piperidinyl-8,8-dipropyl-2-azaspiro[4.5]-decane for 2-(4-Piperidinyl)-8,8-dipropyl-2-azaspiro[4.5]-decane; mp 332°–334° C.

EXAMPLE 3

2-(4-Piperidinyl)-8,8-diethyl-2-azaspiro[4.5]-decane dihydrochloride

The title compound is prepared according to Example 1 (i-iv) by substituting 4,4-diethylcyclohexane-1-carboxy-1-acetic acid anhydride for 4,4-dipropylcyclo-hexane-1-carboxy-1-acetic acid anhydride; mp 331°–332° C.

EXAMPLE 4

2-(2-(4-Imidazolyl)ethyl)-8,8-dipropyl-2-azaspiro[4.5]decane dihydrochloride (i) 2-(2-(4-Imidazolyl)ethyl)-8,8-dipropyl-2-azaspiro [4.5]decane The title compound is prepared according to Example 1 (i-iii) by substituting histamine for 4-amino-1-benzylpiperidine.

(ii) 2-(2-(4-Imidazolyl)ethyl)-8,8-dipropyl-2-azaspiro [4.5]decane dihydrochloride 2-(2-(4-Imidazolyl)ethyl)-8,8-dipropyl-2-azaspiro[4.5] decane was dissolved in a minimum amount of ethanol and a solution of HCl(g)/EtOH was added. The dihydrochloride did not precipitate. The solution was concentrated to dryness and placed in a vacuum oven overnight at 60°/5 mm to give the desired dihydrochloride salt as a white solid: yield 72%; m.p. 258°–262° C.

EXAMPLE 5

2-(3R-pyrrolidinyl)-8,8-dipropyl-2-azaspiro[4.5]-decane dimaleate (i) 2-(3R-pyrrolidinyl)-8,8-dipropyl-2-azaspiro[4.5]-decane-1,3-dione To a solution of 4,4-dipropylcyclohexane-1-carboxy-1-acetic acid anhydride (1 molar equivalent) in xylene was added 3R-aminopyrrolidine (1 molar equivalent). The reaction mixture was heated at reflux with a Dean-Stark trap until 1 equivalent of water was collected in the trap. The reaction mixture was cooled to room temperature and concentrated under reduced pressure to give a viscous, dark brown oil. The crude product was dissolved in methanol and a methanol solution containing maleic acid (1 molar equivalent) was added. The volatiles were stripped off under reduced pressure from the product-maleate solution to yield a dark brown solid. The solid was recrystallized from dichloromethane/ethyl acetate to afford the pure salt as a white crystalline solid. The product salt was solubilized in a minimum of water and the resulting solution basified with 1 M sodium hydroxide and extracted with ethyl ether. The ether extracts were combined, dried over sodium sulfate, filtered, and concentrated to give the desired imide as a viscous oil; 70–75% yield.

(ii) 2-(3R-pyrrolidinyl)-8,8-dipropyl-2-azaspiro[4.5]-decane

To a mixture of lithium aluminum hydride (3.2 molar equivalents) in ethyl ether was added dropwise a solution of 2-(3R-pyrrolidinyl)-8,8-dipropyl-2-azaspiro[4.5]-decane-1,3-dione (1 molar equivalent) in ethyl ether. The reaction mixture was stirred for 2–6 h after addition was completed. The excess hydride was quenched with sodium sulfate-decahydrate and the resulting mixture was filtered. The filtrate was concentrated under reduced pressure to give the diamine as a viscous, colorless oil; 80–85% yield.

(iii) 2-(3R-pyrrolidinyl)-8,8-dipropyl-2-azaspiro[4.5]-decane dimaleate 2-(3R-pyrrolidinyl)-8,8-dipropyl-2-azaspiro[4.5]-decane was dissolved in methanol and a methanol solution containing maleic acid (2 molar equivalents) was added. The solvent volume was reduced under vacuum. A 10% hexane in ethyl acetate solution was carefully added to the product-methanol solution to form a white precipitate which was isolated by filtration. The white solid product required no further purification; mp 168.5°–170° C.; 70–80% yield.

EXAMPLE 6

2-(3S-pyrrolidinyl)-8,8-dipropyl-2-azaspiro [4.5]-decane dimaleate

The title compound is prepared according to Example 5 (i-iii) by substituting 3S-aminopyrrolidine for 3R-aminopyrroldine; mp 169.5°–170.5° C.

EXAMPLE 7

2-(3'-Quinuclidinyl)-8,8-dipropyl-2-azaspiro[4.5]-decane dihydrochloride (i) 2-(3'-Quinuclidinyl)-8,8-dipropyl-2-azaspiro[4.5]decane-1,3-dione To a solution of 4,4-dipropylcyclohexane-1-carboxy-1-acetic acid anhydride (1 molar equivalent) in toluene was added 3-aminoquinuclidine (1 molar equivalent). The reaction mixture was heated to reflux with stirring using a Dean-Stark trap until the volume of water collected was unchanged (approximately five hours), and then allowed to cool. The toluene was evaporated under reduced pressure and the residue partitioned between ethyl acetate and 1N sodium hydroxide solution. The organic phase was separated, washed with water, dried (MgSO$_4$) and evaporated to give 2-(3-quinuclidinyl)-8,8-dipropyl-2-azaspiro[4.5]decane-1,3-dione (94%) as a yellow oil which solidified on standing. This was used without further purification.

(ii) 2-(3'-Quinuclidinyl)-8,8-dipropyl-2-azaspiro [4.5]decane

To a stirred suspension of lithium aluminum hydride (3.5 molar equivalents) in the THF (80 ml) at 0° C. under argon was added a solution of 2-(3'-quinuclidinyl)-8,8-dipropyl-2-azaspiro [4.5]decane-1,3-dione (1 molar equivalent) in THF dropwise over 45 minutes. The reaction mixture was allowed to warm to room temperature then stirred overnight. Sodium sulfate decahydrate was added slowly in portions to quench the unreacted LAH and the resulting suspension of solids was filtered and the filtrate evaporated under reduced pressure to yield a residual colorless oil.

(iii) 2-(3'-Quinuclidinyl)-8,8-dipropyl-2-azaspiro[4.5]decane dihydrochloride 2-(3'-Quinuclidinyl)-8, 8-dipropyl-2-azaspiro[4.5]decane was dissolved in a small volume of ethanol and a solution of saturated hydrogen chloride in ethanol was added. Upon addition of a large volume of ether a white precipitate formed which was filtered and dried giving the title compound (yield 70%) as a white amorphous solid; mp 277°–278° C. Elemental analysis suggest that the title compound was isolated as the monohydrate.

EXAMPLE 8

2-(3'-α-(8'-Methyl-8-azabicyclo(3.2.1)-8,8-dipropyl-2-azaspiro[4.5]decane dihydrochloride (i) 3-α-Amino-8-methyl-8-azabicyclo(3.2.1)octane (3-α-aminotropane)

A solution of tropinone (5.0 g) in ethanol containing palladium on activated carbon (10%, 2.0 g) was saturated with ammonia at 0° C. then hydrogenated on a Parr apparatus at 50 psi for 24 hours. The mixture was filtered through celite and evaporated under reduced pressure. The colorless residual oil was used without further purification.

The above amine (0.5 g) in methanol (5 ml) was treated with 1 ml of phenyl isothiocyanate. After stirring for 30 minutes and triturating with ether, a crystalline solid precipitated which was filtered off and recrystallized from ethyl acetate. The thioureide melted at 156°–157° C. (A. Stoll, E. Tucker and A. Ebnother, Helv. Chim. Acta 38, 559 (1955) and S. Archer, T. R. Lewis and M. J. Unser, J. Am. Chem. Soc. 79, 4194 (1957) report melting points of the endo thioureide as 153°–154° C. and 160°–161° C., respectively.)

(ii) 3-β-Amino-8-methyl-8-azabicyclo(3.2.1)octane (3β-aminotropane)

Prepared by sodium/amyl alcohol reduction of tropinone oxime (M. S. Hadley and F. D. King U.S. Pat. No. 4,273,778 for exact procedures).

The corresponding β-aminotropane thioureide melted at 178°–179° C. (R. Willstatter and W. Moller Ber., 31, 1202 (1898) and S. Arther, T. R. Lewis and M. J. Unser, J. Am. Chem. Soc. 79, 4194 (1957) report melting points of 171°–172° C. and 173°–175° C., respectively)

(iii) 2-(3'-α-(8'-Methyl-8'-azabicyclo(3.2.1)-octane)-8,8-dipropyl-2-azaspiro[4.5]decane dihydrochloride The title compound is prepared according to Example 7 (i-iii) by substituting 3-β-Amino-8-methyl-8-azabicyclo(3.2.1)octane (3β-aminotropane) for 3-aminogainaclidine. The dihydrochloride was isolated as described in Example 11; yield 60% as a white amorphous solid; m.p. 234°–235° C. in 60% yield. Elemental analyses suggest that the title compound was isolated as the monohydrate.

EXAMPLE 9

2-(3'β-8'-Methyl-8'-azabicyclo(3.2.1)-octane)-8,8-dipropyl-2-azaspiro[4.5]decane-dihydrochloride The title compound is prepared according to Example 1 (i-iv) by substituting 3-β-aminotropane for 3-αaminotropane. The dihydrochloride was isolated as a white amorphous solid; m.p. 245°–247° C. Elemental analyses suggest that the title compound was isolated as the monohydrate.

EXAMPLE 10

2-(4-Piperidinyl)-9,9-dipropyl-3-azaspiro[4.5]-decane dihydrochloride

The title compound is prepared according to Example 1 (i-iv) by substituting 4,4-dipropylcyclohexane-1,1-diacetic acid anhydride for 4,4-dipropylcyclohexane-1-carboxy-1-acetic acid anhydride.

II. Composition Examples

EXAMPLE 11

CAPSULE COMPOSITION

A pharmaceutical composition of this invention in a form of a capsule is prepared by filling a standard two-piece hard gelatin capsule with the mixture of 50 mg of a compound of Formula (I), in powdered form, 110 mg of lactose, 32 mg of talc and 8 mg of magnesium stearate.

EXAMPLE 12

INJECTABLE PARENTERAL COMPOSITION

A pharmaceutical composition of this invention in a form suitable for administration by injection is prepared by dispersing 1.5% by weight of a compound of Formula (i) in 10% by volume propylene glycol and water.

EXAMPLE 13

OINTMENT COMPOSITION

Compound of Formula (I) 1.0g

White soft paraffin to 100.0 g

The compound of Formula (I) is dispersed in a small volume of the vehicle and gradually incorporated into the bulk of the vehicle to produce a smooth, homogeneous product. Collapsible metal tubes are then filled with the dispersion.

EXAMPLE 14

TOPICAL CREAM COMPOSITION

| | |
|---|---|
| Compound of Formula (I) | 1.0 g |
| Polawax GP 200 | 20.0 g |
| Lanolin Anhydrous | 2.0 g |
| White Beeswax | 2.5 g |
| Methyl hydroxybenzoate | 0.1 g |
| Distilled Water to | 100.0 g |

The polawax, beeswax and lanolin are heated together at 60° C. A solution of methyl hydroxybenzoate is added and homogenization is achieved using high speed stirring. The temperature is then allowed to fall to 50° C. The compound of Formula (I) is then added and dispersed throughout, and the composition is allowed to cool with slow speed stirring.

EXAMPLE 15

TOPICAL LOTION COMPOSITION

| | |
|---|---|
| Compound of Formula (I) | 1.0 g |
| Sorbitan Monolaurate | 0.6 g |
| Polysorbate 20 | 0.6 g |

-continued

| Cetostearyll Alcohol | 1.2 g |
| Glycerin | 6.0 g |
| Methyl Hydroxybenzoate | 0.2 g |
| Purified Water to | 100.0 ml |

The methyl hydroxybenzoate and glycerin are dissolved in 70 ml of the water at 75°. The sorbitan monolaurate, polysorbate 20 and cetostearryl alcohol are melted together at 75° C. and added to the aqueous solution. The resulting emulsion is homogenized, allowed to cool with continuous stirring and the compound of Formula (I) is added as a suspension in the remaining water. The whole suspension is stirred until homogenized.

EXAMPLE 16

EYE DROP COMPOSITION

| Compound Formula (I) | 0.5 g |
| Methyl Hydroxybenzoate | 0.01 g |
| Propyl Hydroxybenzoate | 0.04 g |
| Purified Water to | 100.00 ml |

The methyl and propyl hydroxybenzoates are dissolved in 70 ml purified water at 75° C. and the resulting solution is allowed to cool. The compound of Formula (I) is then added, and the solution is sterilized by filtration through a membrane filter (0.22 mu m pore size) packed aseptically into suitable sterile containers.

EXAMPLE 17

COMPOSITION FOR ADMINISTRATION BY INHALATION

For an aerosol container with a capacity of 15–20 ml: Mix 10 mg of a compound of Formula (I) with 0.2–0.2% of a lubricating agent, such as polysorbate 85 or oleic acid, and disperse such mixture in a propellant, such as freon, preferably in a combination of (1,2 dichlorotetrafluoroethane) and difluorochloromethane and put into an appropriate aerosol container adapted for either intranasal or oral inhalation administration.

EXAMPLE 18

COMPOSITION FOR ADMINISTRATION BY INHALATION

For an aerosol container with a capacity of 15–20 ml: Dissolve 10 mg of a compound of Formula (I) in ethanol (6–8 ml), add 0.1–0.2% of a lubricating agent, such as polysorbate 85 or oleic acid; and disperse such in a propellant, such as freon, preferably a combination of (1,2-dichlorotetrafluoroethane) and difluorochloromethane, and put into an appropriate aerosol container adapted for either intranasal or oral inhalation administration.

EXAMPLE 19

TABLET COMPOSITION

A pharmaceutical composition of this invention in the form of a tablet is prepared by granulating a mixture of; 50 mg of a compound of Formula (I), in powdered form, 100 mg of calcium sulfate dihydrate, 10 mg of sucrose, 5 mg of starch, 3 mg of talc and 1 mg of stearic acid with a 10% gelatin solution. The wet granules are screened dried, mixed with the starch, talc and stearic acid, screened and compressed into a tablet.

What is claimed is:

1. A compound of the Formula:

in which:

$R^1$ and $R^2$ are the same or different and are selected from hydrogen or straight chain, branched chain or cyclic alkyl, provided that the total number of carbon atoms contained by $R^1$ and $R^2$ when taken together is 4–10; or $R^1$ and $R^2$ are joined together to form a cyclic alkyl group containing 3–7 carbon atoms;

A is absent or present as $C_1$–$C_7$ alkylene; and $R^3$ is a heterocyclic ring selected from; pyrrolidine, piperidine, imidazole, and azabicyclo(3.2.1), wherein said heterocyclic ring is bonded through a carbon atom thereof and wherein each nitrogen atom of said heterocyclic ring is optionally substituted by a substituent selected from; hydrogen, —$CH_3$, —$CH_2$—$CH_3$, and —$CH_2$—$CH_2$—$CH_3$, —$CH(CH_3)_2$; provided that such nitrogen atoms are not substituted when they form part of a double bond or when they are attached to three carbon atoms in a azabicyclo(3.2.1.) ring system; or a pharmaceutically acceptable salt, hydrate or solvate thereof.

2. A compound of claim 1 wherein:

$R^1$ and $R^2$ are each independently $C_2$ or $C_3$ alkyl;

A is absent or present as $C_1$–$C_2$ alkylene; and $R^3$ is a heterocyclic ring selected from; pyrrolidine, piperidine, imidazole, and azabicyclo(3.2.1),wherein said heterocyclic ring is bonded through a carbon atom thereof and wherein each nitrogen atom of said heterocyclic ring is optionally substituted by a substituent selected from; hydrogen, —$CH_3$, —$CH_2$—$CH_3$, and —$CH_2$—$CH_2$—$CH_3$; provided that such nitrogen atoms are not substituted when they form part of a double bond or when they are attached to three carbon atoms in a azabicyclo(3.2.1.) ring system; or a pharmaceutically acceptable salt, hydrate or solvate thereof.

3. A compound of claim 2 wherein:

$R^1$ and $R^2$ are each independently $C_2$ or $C_3$ alkyl;

A is absent or present as $C_1$–$C_2$ alkylene; and $R^3$ is a heterocyclic ring selected from; pyrrolidine, piperidine, imidazole and azabicyclo(3.2.1), wherein said heterocyclic ring is bonded through a carbon atom thereof and wherein each nitrogen atom of said heterocyclic ring is optionally substituted by a substituent selected from; hydrogen, and —$CH_3$; provided that such nitrogen atoms are not substituted when they form part of a double bond or when they are attached to three carbon atoms in a azabicyclo(3.2.1.) ring system; or a pharmaceutically acceptable salt, hydrate or solvate thereof.

4. The compound of claim 3 which is

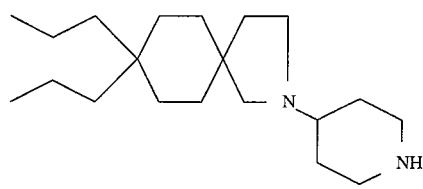

or a pharmaceutically acceptable salt, hydrate or solvate thereof.

5. The compound of claim 2 which is

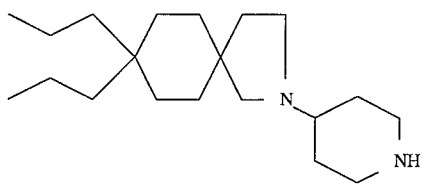

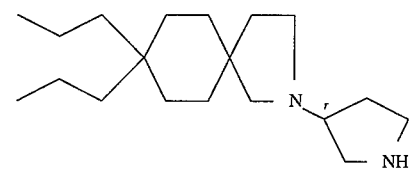

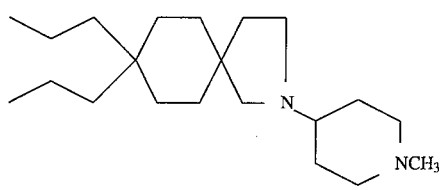

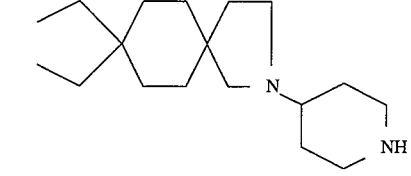

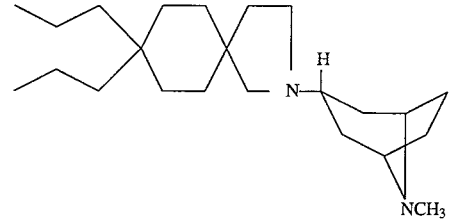

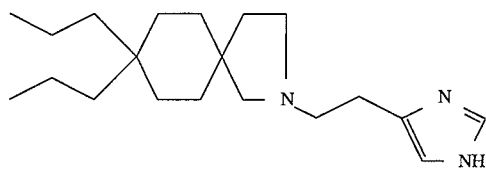

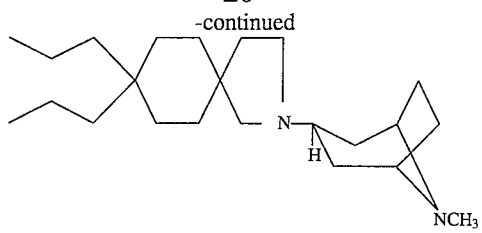

or

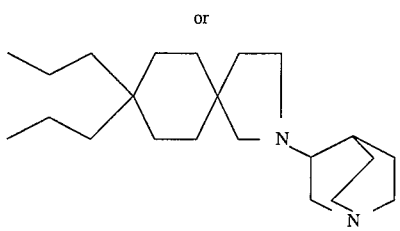

or a pharmaceutically acceptable salt, hydrate or solvate thereof.

6. A pharmaceutical composition comprising a pharmaceutically acceptable carrier or diluent and a compound of claim 1.

7. The composition of claim 6 wherein the compound is:

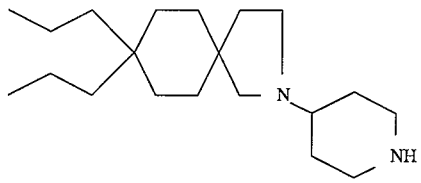

or a pharmaceutically acceptable salt, hydrate or solvate thereof.

8. The composition of claim 6 wherein the compound is selected from:

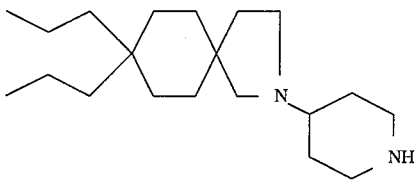

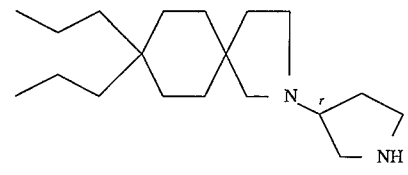

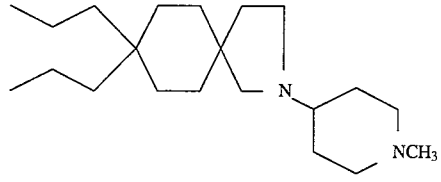

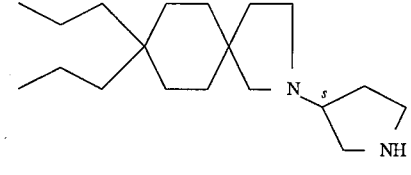

21
-continued
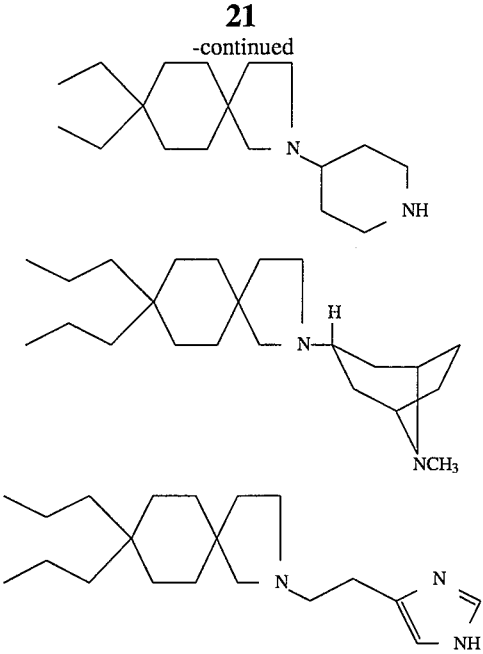
22
-continued
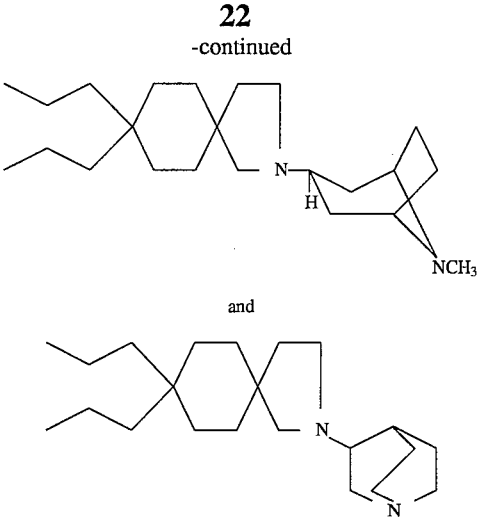
or a pharmaceutically acceptable salt, hydrate or solvate thereof.
* * * * *